United States Patent
Macedo (10) Patent No.: US 7,122,238 B2
(45) Date of Patent: Oct. 17, 2006

(54) CLEANSING ARTICLE FOR PERSONAL CARE

(75) Inventor: Filomena Augusta Macedo, Naugatuck, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 30 days.

(21) Appl. No.: 10/958,788

(22) Filed: Oct. 5, 2004

(65) Prior Publication Data

US 2006/0013995 A1    Jan. 19, 2006

(51) Int. Cl.
- B32B 3/10 (2006.01)
- A61K 6/00 (2006.01)
- A61F 13/00 (2006.01)
- B08B 1/00 (2006.01)

(52) U.S. Cl. .............. 428/136; 424/401; 424/443; 15/104.93; 15/209.1

(58) Field of Classification Search ............ 428/137, 428/138, 156, 172, 187; 424/401, 443; 15/104.43, 15/209.1
See application file for complete search history.

(56) References Cited

U.S. PATENT DOCUMENTS

| | | | |
|---|---|---|---|
| 5,951,991 A | 9/1999 | Wagner et al. | |
| 5,980,931 A | 11/1999 | Fowler et al. | |
| 6,267,975 B1 | 7/2001 | Smith, III et al. | |
| 6,280,757 B1 | 8/2001 | McAtee et al. | |
| 6,378,698 B1 | 4/2002 | Scoggins | |
| 6,638,527 B1 * | 10/2003 | Gott et al. | 424/443 |
| 6,730,621 B1 | 5/2004 | Gott et al. | |
| 2001/0018068 A1 | 8/2001 | Lorenzi et al. | |
| 2001/0046513 A1* | 11/2001 | Gott et al. | 424/443 |
| 2002/0177827 A1* | 11/2002 | Noda et al. | 604/364 |
| 2003/0206940 A1 | 11/2003 | Gott et al. | |
| 2003/0228351 A1* | 12/2003 | Hasenoehrl et al. | 424/443 |

FOREIGN PATENT DOCUMENTS

| | | |
|---|---|---|
| DE | 101 18 775 | 4/2001 |
| GB | 2362813 A | 12/2001 |
| WO | 94/11482 | 5/1994 |
| WO | 02/36084 A2 | 5/2002 |
| WO | 2005/007789 A3 | 1/2005 |

OTHER PUBLICATIONS

International Search Report, Feb. 10, 2005.
International Search Report, Jun. 10, 2005.

* cited by examiner

Primary Examiner—Donald J. Loney
(74) Attorney, Agent, or Firm—Milton L. Honig (57) ABSTRACT

A disposable personal care cleansing article is provided having a cleansing composition adjacent to a water insoluble substrate formed of a fibrous web. A plurality of slits having a length ranging from about 6 to 40 mm are cut into the web. The slits allow the article to expand when a consumer applies the article to cleanse the body under a flow of water.

14 Claims, 4 Drawing Sheets

CLEANSING ARTICLE FOR PERSONAL CARE

BACKGROUND OF THE INVENTION

1. Field of the Invention

The invention concerns disposable single use, surfactant impregnated cleansing articles.

2. The Related Art

Personal cleansing and conditioning products have traditionally been marketed in a variety of forms such as bar soaps, creams, lotions, and gels. These formulations have attempted to satisfy a number of criteria to be acceptable to consumers. These criteria include cleansing effectiveness, skin feel, skin mildness and lather volume. Ideal personal cleansers should gently cleanse the skin or hair, cause little or no irritation, and not leave the skin or hair overly dry after frequent use.

New delivery forms have in the last several years appeared on the market. Many of these are based on the use of a textile or wiping article. These products are often substantially dry or damp woven or non-woven cloth upon which is deposited a cleansing composition of surfactant, structurant, skin conditioning agent and other performance ingredients.

Disposable single use articles are convenient because they represent a more sanitary alternative to use of a sponge, washcloth, or other cleansing implement intended for multiple reuse. The disposable implements avoid bacterial growth, unpleasant odors and other undesirable characteristics related to repeated use.

Illustrative of the wiping article technology is U.S. Pat. No. 6,730,621 B1 (Gott et al.) disclosing a disposable substantially damp cleansing article with amounts of water ranging from greater than 15% to no higher than about 40% by weight of the total article. "Substantially dry" wiping articles are reported in U.S. Pat. No. 5,951,991 (Wagner et al.) which focuses upon providing a substrate (i.e. textile) with a conditioning emulsion separately impregnated from the lathering surfactant onto the substrate. U.S. Pat. No. 5,980,931 (Fowler et al.) emphasizes impregnation of oil soluble conditioning agents.

Still further technology is found in U.S. Pat. No. 6,280,757 B1 (McAtee et al.) which describes disposable, personal cleansing articles wherein the substrate contains a plurality of apertures ranging in size from about 0.5 to 5 mm in diameter. These apertures are located within the cleansing surface of the substrate at a frequency of from about 0.5 to 12 apertures per linear centimeter.

A problem with some of the known disposable cleansing wipe technology is that when wetted with substantial water, the substrate tends to shrink into a "ball configuration" within a user's hand. Shrinkage is undesirable because the system becomes less efficient in functioning to wipe large surfaces. This is especially so with respect to articles intended for cleaning the larger body beyond merely facial areas.

Accordingly, the present invention seeks to overcome the problems of "ball-up" of textiles in the context of body cleansing.

SUMMARY OF THE INVENTION

A personal care cleansing article is provided which includes:

(i) a water insoluble substrate formed of a web with a plurality of slits having a length ranging from about 6 to about 40 mm and a width no larger than about 2 mm; and (ii) a cleansing composition adjacent the substrate comprising from about 0.1% to about 95% of lathering surfactants by weight of the composition.

BRIEF DESCRIPTION OF THE DRAWINGS

Further features and advantages of the present invention will become more evident from consideration of the following drawing in which.

DETAILED DESCRIPTION OF THE INVENTION

Now it has been found that earlier problems with apertured personal care cleansing articles can be overcome using a web patterned with elongated slits. By contrast to round or substantially round apertures, the slits cause the article to spread outward when wetted with flows of water. Expansion of the article allows a user more wiping surface area, especially when bathing larger surfaces of the human torso. The article is simply more efficient with the slitted web than with ordinary round apertures.

Figure 1:
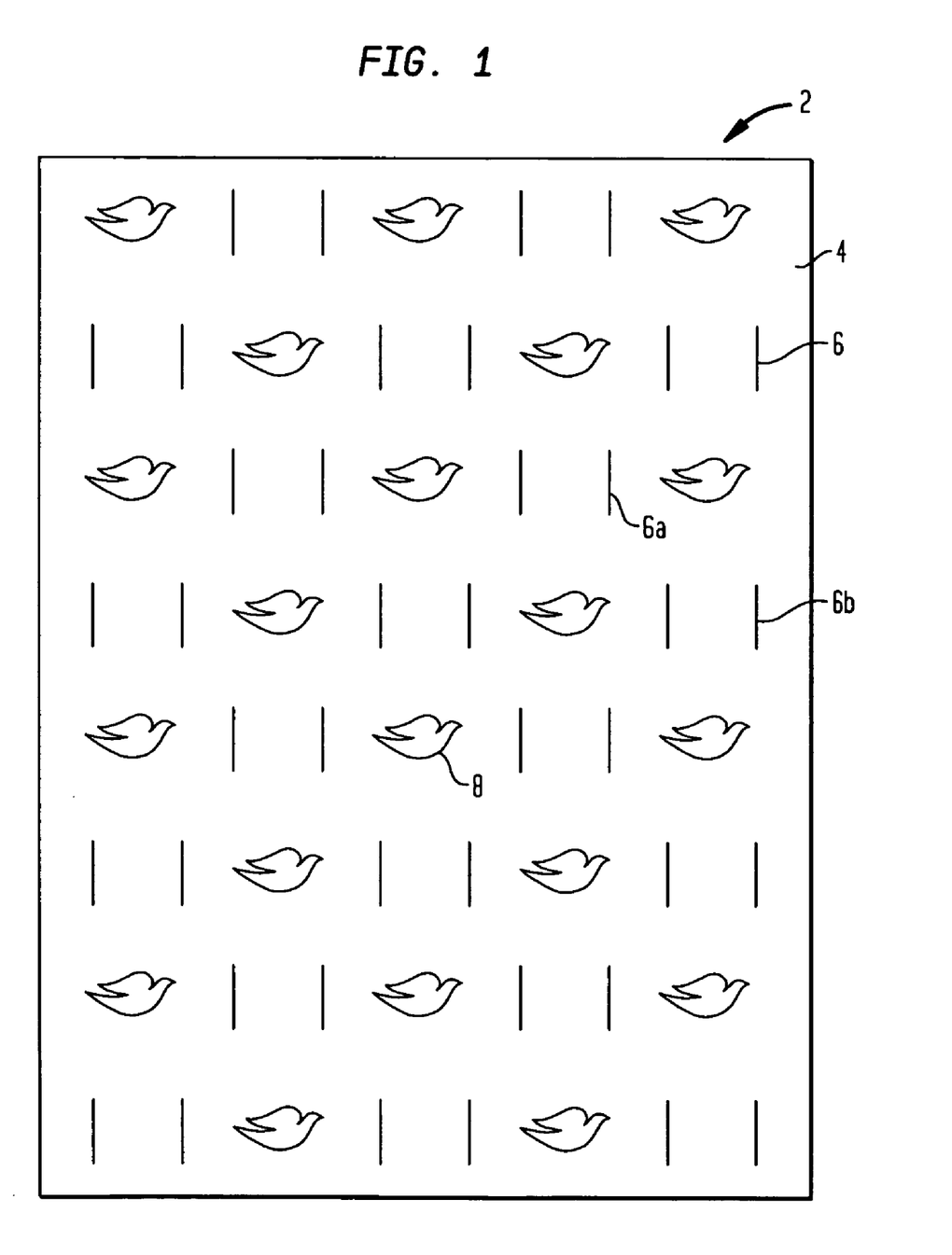
FIG. 1 is a top plan view of a first embodiment of an article of an article according to the present invention.

FIG. 1 illustrates a first embodiment of the present invention. A substrate 2 is shown formed as a web 4. A series of slits 6 are cut into and through the web. These slits are linear elongate structures oriented in a length direction of the web. Rows of the slits 6a and 6b alternate in staggered slit configuration. More particularly, each of the four slits in row 6a are offset along a width direction of the web from the slits of row 6b. An icon 8 is printed or alternatively pressure embossed into the web 4. Embossment is particularly useful; the compressed icon or logo serves as a point of resistance in instances where the slit might tend to tear. Cleansing composition is impregnated onto the web, preferably as a uniform coating over the whole surface. Alternatively, the cleansing composition can be coated in particular areas of the web such as in a striped pattern along a length thereof.

The slits in FIG. 1 are forty in number. However, the plurality of slits according to the present invention may range anywhere from about 4 to about 500, preferably from about 10 to about 100, more preferably from about 20 to about 80, optimally from about 30 to about 50 per substrate. Area of the substrate may range from about 25 to about 2,500 $cm^2$, preferably from about 100 to 800 $cm^2$, optimally from about 250 to about 500 $cm^2$. Slit lengths may range from about 6 to about 40 mm, preferably from about 10 to about 25 mm.

Figure 2:
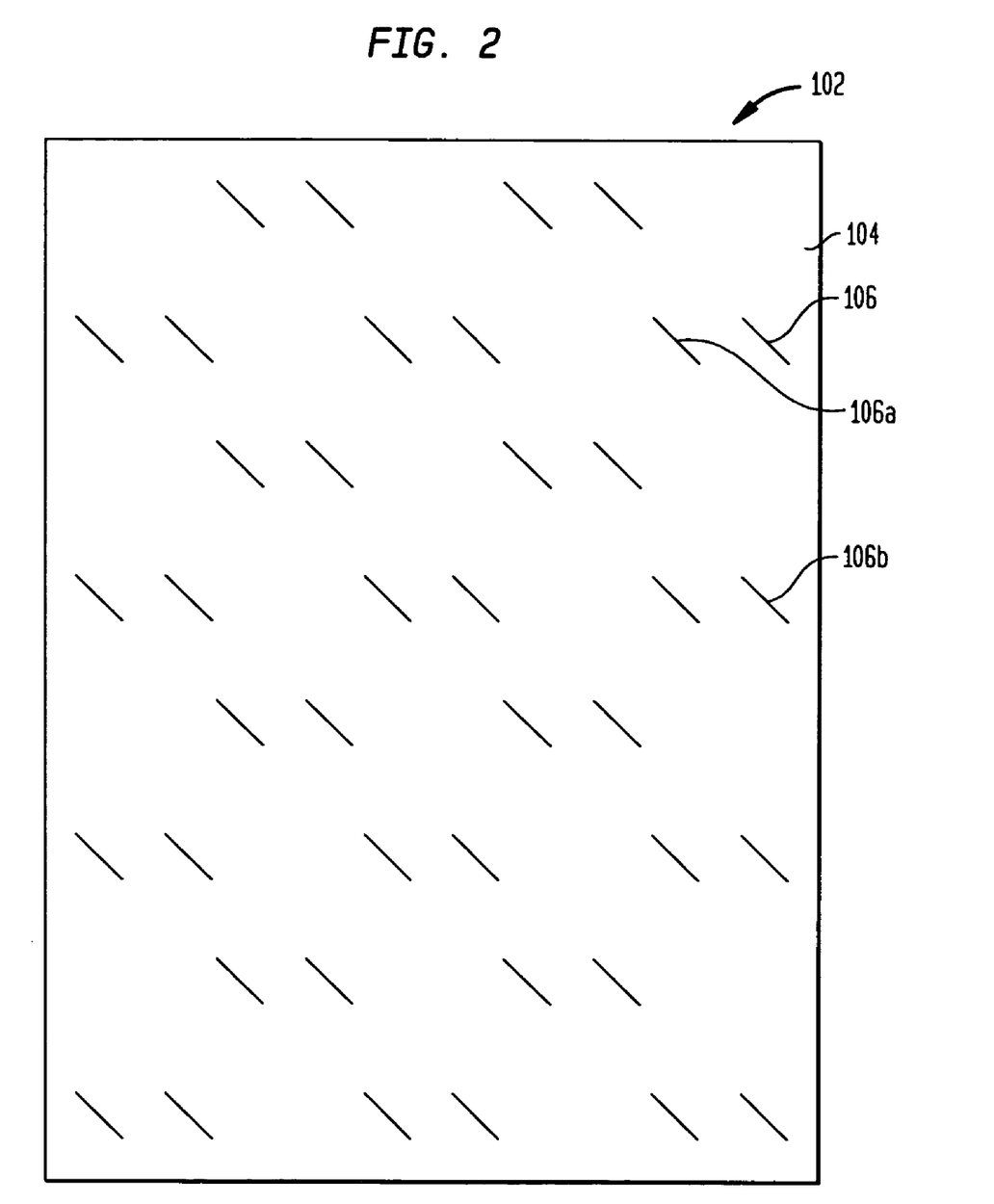
FIG. 2 is a top plan view of a second embodiment of an article according to the present invention.

FIG. 2 illustrates a second embodiment of the present invention. Substrate 102 is formed of a web 104. A series of slanted slits 106 are cut through web 104. These slits are oriented at an oblique angle to a length of the web. The angle may range from about 5 to about 90° relative to an axis defining a length of the web. Adjacent rows of slits 106a and 106b stagger individual slits to avoid mirror image cuts. The staggered arrangement prevents the web from readily tearing during use. Although not shown, it is envisioned that webs can be formed with slits that are angled in different directions.

Figure 3:
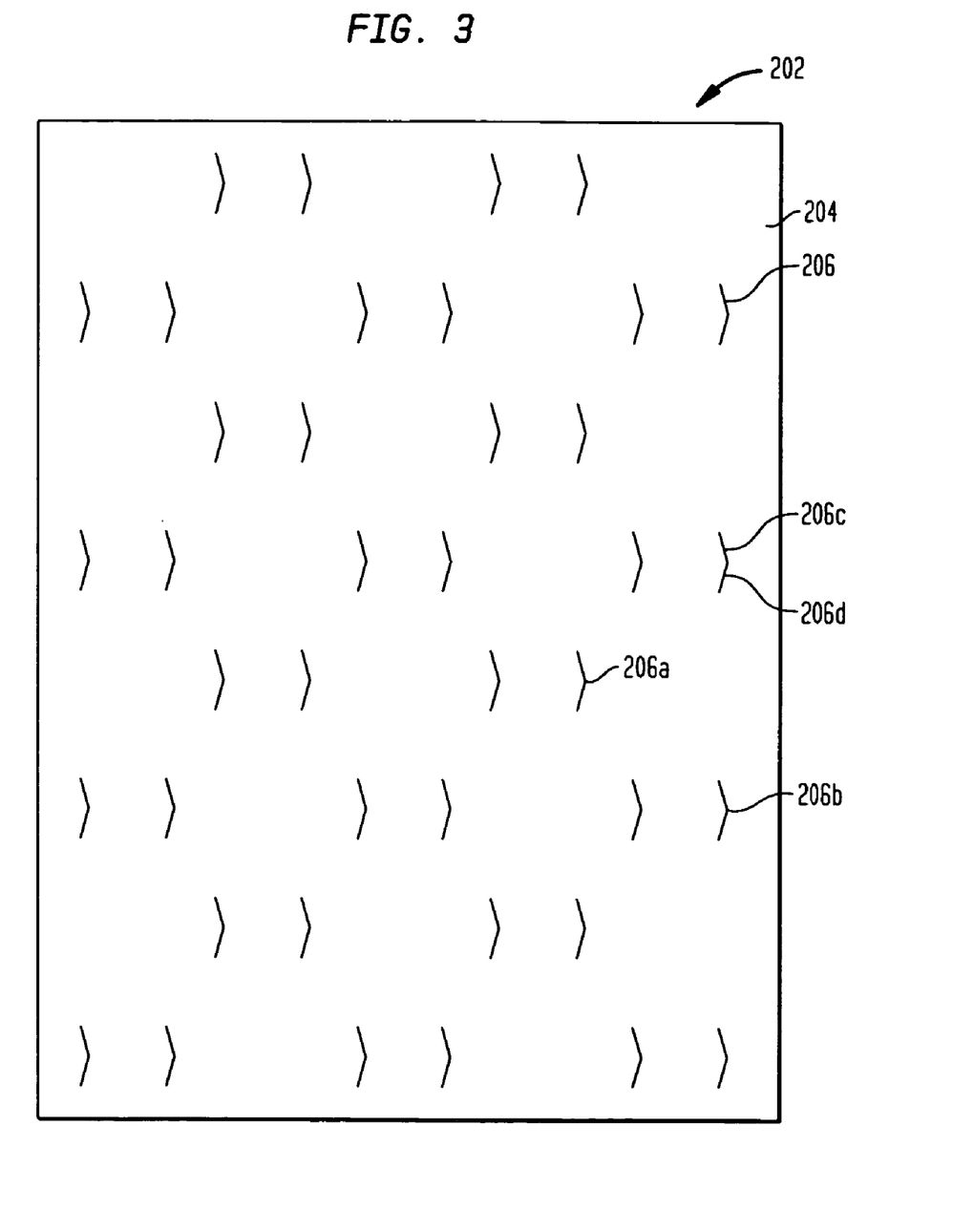
FIG. 3 is a top plan of a third embodiment of an article according to the present invention.

FIG. 3 illustrates a third embodiment of the present invention. Therein is shown a substrate 202 formed from a web 204. Slits 206 are cut through the web. These slits are defined by arm members 206c and 206d, the arm members being oriented at an angle of approximately 90°. In other embodiments of the sawtooth configuration, the angle between the arm members of a slit may range from about 10 to about 150, more preferably from about 60 to about 110° of arc. Although FIG. 3 illustrates a single sawtooth slit 206, it is also possible to have multi sawtooth configurations within a single slit. For purposes of identifying the length dimension of a slit, this is considered to be the distance from the end of one arm member to the furthest point of the other arm member. In the embodiment of FIG. 3, adjacent rows of slits 206a and 206b are in staggered slit configuration to prevent shredding or ripping of the web.

Figure 4:
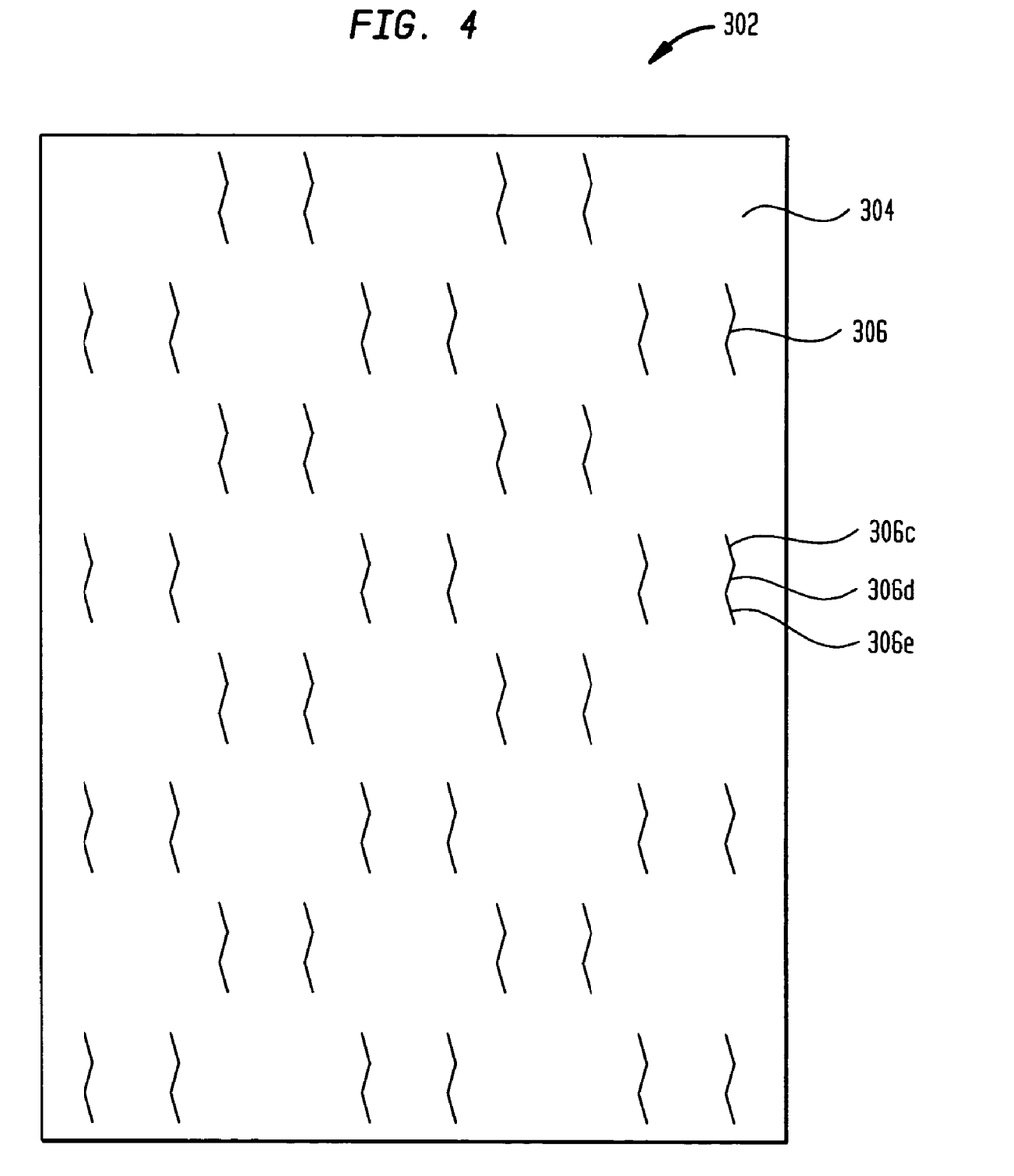
FIG. 4 is a top plan of a fourth embodiment of an article according to the present invention.

FIG. 4 illustrates a fourth embodiment of the present invention. Therein is shown a substrate 302 formed from a web 304. Slits 306 are cut through the web in a zigzag or "Z" manner. These slits have arm members 306c, 306d and 306e. This embodiment is the simplest of the aforementioned multi sawtooth configuration.

A necessary element of the present invention is that of a water insoluble substrate. By "water insoluble" is meant the substrate does not dissolve or readily break apart upon immersion in water. A wide variety of materials can be used as the substrate. The following non-limiting characteristics are desirable: (i) sufficient wet strength for use, (ii) sufficient abrasivity, (iii) sufficient loft and porosity, (iv) sufficient thickness, and (v) appropriate size.

Non-limiting examples of suitable insoluble substrates which meet the above criteria include fibered non-woven substrates, woven substrates, hydro-entangled substrates, air entangled substrates and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or by-products. By synthetic is meant that the materials are obtained primarily from various man-made materials or from material that is usually a fibrous web comprising any of the common synthetic or natural textile-length fibers, or mixtures thereof.

Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof.

Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, and Nylon 610); polyesters such as Fortrel®, Kodel®, and Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers.

Most preferred as a substrate for purposes of this invention are non-woven substrates, especially blends of rayon/polyester in ratios of 10:90 to 90:10, preferably ratios of 20:80 to 80:20, optimally 40:60 to 60:40 by weight. A most useful substrate is a needle punched web formed of 87.5% polyester/12.5% Tencel® available from Texel Inc., Quebec, Canada. Tencel® is a cellulose based fiber.

Especially useful for the present invention are fibrous batting webs which are highloft in nature. In a preferred embodiment, the web may have Loft-Soft Ratio of greater than about 1.1. In other words, the fibrous web of the invention preferably is lofty and fluid-permeable.

As used herein, "lofty" means that the layer has density of from about 0.01 g/cm$^3$ to about 0.00005 g/cm$^3$ and a thickness of from about 0.1 to about 7 cm.

Loftiness of substrates and softness of substrates are related. Softness has several independent, contributing components. One component is a kind of "pillowy" softness. That is, when a force is applied by hand or finger pressure, the substrate easily compresses in much the same way a pillow compresses under pressure to support a body member resting thereon. The web of the present invention is preferably characterized by having a Loft-Soft Ratio of greater than about 1.1, more preferably greater than about 1.3, and most preferably greater than about 1.5.

The methodology for assessing Loft-Soft Ratio is as follows. Substrate samples are cut using a 4.7 cm diameter punch and hammer. In instances where the punching process inelastically compresses edges of discs, the edges are carefully fluffed to restore original dimension. With the top plate in position, the Instron load cell is calibrated and is then run in compression mode at 1.27 cm/minute rate of descent. The Instron may be controlled manually or by computer as long as the final compression is greater than 30 grams/in$^2$ pressure and data is collected quickly enough (computer assisted recommended) to determine the height at various compression values during descent. The top plate is then moved down until it contacts the base plate at which point the height is set at zero. It is important that the top plate and base plate are parallel, making contact at all points simultaneously.

Once the apparatus is zeroed, the top plate is retracted to a position above the base plate allowing sufficient space to interpose a substrate sample disc. A substrate disc is then placed in the center of the base plate. The Instron is then set to compress each substrate sample once fully. Next, the Instron is turned on and the height and force of the top plate is continuously recorded. Once the compression of the sample is complete, the compression with new samples of the same substrate is repeated as many times as are needed to establish a reliable average. The average height about the base plate at compression values of 5 gms/in$^2$ and 30 gms/in$^2$ equals the thickness at 5 gms/in$^2$ and 30 gms/in$^2$, respectively. The Loft-Soft Ratio is then calculated as the ratio of the thickness at 5 gms/in$^2$ divided by the thickness at 30 gms/in$^2$.

Anywhere from 1 to 100, preferably from 5 to 50 wipe articles may be stored within a dispensing pouch or container, preferably a moisture impermeable pouch or container. During storage and between dispensing, the pouch or container is preferably resealable. Single wipe containing pouches may also be employed.

The water insoluble substrates of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the user to further distinguish the surfaces.

Although the present invention may be suitable for substrates with two or more layers having different texture and abrasiveness, the best effectiveness of the present invention can be found with single or multiple layered substrates of identical construction. Different textures can be imparted to a unitary layer of nonwoven by having a higher denier formed on one surface than on the other. This may be achieved in a needle punch process through carding low denier fibers separately from higher denier fibers. The result is a non-homogeneous arrangement of fiber sizes. Alternatively, a relatively abrasive side can be achieved by utilizing two different fiber types in the nonwoven, more of one type than another being directed to a particular side of the substrate through carding and needle punching these together. A still further method of achieving a relatively abrasive and a softer side is by coating one surface of the substrate with polymers.

The amount of cleansing composition relative to the substrate may range from about 20:1 to 1:20, preferably from 10:1 to about 1:10 and optimally from about 2:1 to about 1:2 by weight.

An essential element of compositions according to the present invention is that of a lathering surfactant. By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair, and yet meet the lathering criteria described above.

The products of the present invention typically include at least one lathering surfactant in an amount from about 0.1% to about 95%, preferably from about 0.75% to about 40%, and more preferably from about 1% to about 20%, based on the weight of the impregnated composition. Total of lathering surfactants will be present in amount from about 0.1% to about 95%, preferably from about 5% to about 70%, optimally from about 10% to about 50% by weight of the cleansing compositions.

A wide variety of lathering surfactants are useful herein and include those selected from the group consisting of anionic, nonionic, cationic, amphoteric and lathering surfactant mixtures thereof.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3^- M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40®.

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3^- M+)CO_2R^2$ where $R^1$ is straight or branched alkyl from about $C_8$- to $C_{18}$, preferably $C_{12}$ to $C_{16}$, and $R^2$ is straight or branched alkyl from about $C_1$ to $C_6$, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula $RCON(CH_3)CH_2CH_2CO_2M$ wherein R is alkyl or alkenyl of about 10 to about 20 carbon atoms and M is a water-soluble cation such as ammonium, sodium, potassium and trialkanolammonium. Most preferred is sodium lauroyl sarcosinate.

(12) Alkyl lactylates wherein the alkyl groups range from 8 to 12 carbon atoms, with sodium lauroyl lactylate sold as Pationic 138C® available from the Patterson Chemical Company as the most preferred.

(13) Taurates having from 8 to 16 carbon atoms, with cocoyl methyl taurate being preferred.

Nonionic lathering surfactants suitable for the present invention include $C_{10}$–$C_{20}$ fatty alcohol or acid hydrophobes condensed with from 2 to 100 moles of ethylene oxide or propylene oxide per mole of hydrophobe; $C_2$–$C_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-$C_8$–$C_{20}$ fatty acids; and polyoxyethylene sorbitan available as Polysorbate 80 and Tween 80® as well as combinations of any of the above surfactants.

Other useful nonionic surfactants include alkyl polyglucosides, saccharide fatty amides (e.g. methyl gluconamides) as well as long chain tertiary amine oxides. Examples of the latter category are: dimethyldodecylamine oxide, oleyldi(2-hydroxyethyl)amine oxide, dimethyloctylamine oxide, dimethyldecylamine oxide, dimethyltetradecylamine oxide, di(2-hydroxyethyl)tetradecylamine oxide, 3-didodecyloxy-2-hydroxypropyldi(3-hydroxypropyl)amine oxide, and dimethylhexadecylamine oxide.

Amphoteric lathering surfactants useful for the present invention include aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Illustrative substances are cocamidopropyl betaine, cocamphoacetate, cocamphodiacetate, cocamphopropionate, cocamphodipropionate, cocamidopropyl hydroxysultaine, cetyl dimethyl betaine, cocamidopropyl PG-dimonium chloride phosphate, coco dimethyl carboxymethyl betaine, cetyl dimethyl betaine and combinations thereof.

For purposes of the present invention, the total of all lathering surfactants to water may be in a weight ratio ranging from about 1:10 to about 5:1, preferably from about 1:4 to about 4:1, more preferably from about 1:3 to about 3:1, and optimally from about 1:2 to about 2:1.

Cleansing compositions of the present invention may also include silicones of a volatile and non-volatile variety. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the silicones may range from about 0.01 to about 20%, preferably from about 0.5 to about 3% by weight of the cleansing composition.

Cationic conditioning agents in monomeric and polymeric type are also useful for purposes of this invention. Examples of the polymeric type include: cationic cellulose derivatives, cationic starches, copolymers of a diallyl quaternary ammonium salt and an acrylamide, quaternized vinylpyrrolidone, vinylimidazole polymers, polyglycol amine condensates, quaternized collagen polypeptide, polyethylene imine, cationized silicon polymer (e.g. Amodimethicone), cationic silicon polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, and Jaguar C-16), and quaternary ammonium salt polymers (e.g. Mirapol A-15, Mirapol AD-1 and Mirapol AZ-1).

Examples of monomeric cationic conditioning agents are salts of the general structure:

wherein $R^1$ is selected from an alkyl group having from 12 to 22 carbon atoms, or aromatic, aryl or alkaryl groups having from 12 to 22 carbon atoms; $R^2$, $R^3$, and $R^4$ are independently selected from hydrogen, an alkyl group having from 1 to 22 carbon atoms, or aromatic, aryl or alkaryl groups having from 12 to 22 carbon atoms; and $X^-$ is an anion selected from chloride, bromide, iodide, acetate, phosphate, nitrate, sulfate, methyl sulfate, ethyl sulfate, tosylate, lactylate, citrate, glycolate, and mixtures thereof. Additionally, the alkyl groups can also contain ether linkages, or hydroxy or amino group substituents (e.g. the alkyl groups can contain polyethylene glycol and polypropylene glycol moieties). Preferably the anion is phosphate, especially preferred is hydroxy ethyl cetyl dimonium phosphate available as Luviquat® Mono CP from the BASF Corporation.

Amino silicones quats may similarly be employed. Most preferred is Silquat AD designated by the CTFA as Silicone Quaternium 8, available from Siltech Inc.

Amounts of each cationic agent may range from about 0.05 to about 5%, preferably from about 0.1 to about 3%, optimally from about 0.3 to about 2.5% by weight of the impregnated composition.

Water-binding agents are preferably included in compositions of the present invention. Water soluble binding agents such as polyhydric alcohols are particularly preferred. Typical polyhydric alcohols include glycerol (also known as glycerin), polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the water-binding agent is preferably glycerin. Also particularly preferred are polyethylene glycol (average molecular weight ranging from about 200 to about 2,000,000, with PEG-9M and PEG-14M being preferred) and hexylene glycol. The amount of water-binding agent may range anywhere from about 0.5 to about 50%, preferably between about 1 and about 30% by weight of the composition.

Certain embodiments of the present invention may be substantially dry or even damp. The substantially dry embodiments may have a water content ranging from about 0 to about 15%, preferably from about 10%, optimally no higher than 5% by weight of the article. Damp articles may have a water content ranging from about 20% to about 100%, preferably from about 25% to about 40% by weight of the article. Indeed, personal care articles of this invention operate most efficiently at a water content between about 20 and 40% by weight of the article.

The disposable, single use personal care cleansing products of the present invention are manufactured by separately or simultaneously adding onto or impregnating into a water insoluble substrate the cleansing composition including lathering surfactants and conditioners, wherein the resulting product is substantially dry. By "separately" is meant that the surfactants and the conditioners can be added sequentially, in any order without first being combined together. By "simultaneously" is meant that the surfactants and conditioners can be added at the same time, with or without first being combined together.

The surfactant, conditioners, water-binding agents and any other optional ingredients can be added onto or impregnated into the water insoluble substrate by any means known to those skilled in the art. For example, addition can be through spraying, laser printing, splashing, dipping, soaking, or coating.

Slits may be formed in the web of the substrate either before or after impregnation/deposition of any cleansing composition. Cuts into the web can be achieved by two groups of knives, the first group being offset a short distance from that of the second group. The offset achieves adjacent rows with staggered slits cut into the web. It is preferable that slits of this invention are not curved.

Except in the operating and comparative examples, or where otherwise explicitly indicated, all numbers in this description indicating amounts of material ought to be understood as modified by the word "about".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

The following examples will more fully illustrate the embodiments of this invention. All parts, percentages and proportions referred to herein and in the appended claims are by weight unless otherwise illustrated.

EXAMPLES 1–8

A personal care article according to the present invention is prepared by using a needle punched nonwoven textile of 87.5% polyester/12.5% Tencel® having 12 cm length slits in a pattern shown in FIG. 1. The article is approximately 20 cm in length and 15 cm in width. Thereupon is coated a cleansing composition having a formula outlined under Table I.

TABLE I

| Ingredient | \multicolumn{8}{c}{Example (Weight %)} | | | | | | | |
|---|---|---|---|---|---|---|---|---|
| | 1 | 2 | 3 | 4 | 5 | 6 | 7 | 8 |
| PHASE A | | | | | | | | |
| Soybean Oil | 10.00 | 10.00 | 6.00 | 6.00 | 8.00 | 8.00 | 4.00 | 4.00 |
| 2-Methyl-1,3 Propanediol | 0.50 | 0.50 | 0.50 | 0.50 | 0.50 | 0.50 | 0.50 | 0.50 |
| Cocamide Monoethanolamide | 2.00 | 2.00 | 3.00 | 3.00 | 3.00 | 3.00 | 3.00 | 5.00 |
| Lauric Acid | 2.80 | 1.80 | 1.80 | 1.80 | 1.80 | 1.80 | 1.80 | 1.80 |
| Nonionic Surfactant | 0.25 | 0.25 | 0.25 | 0.25 | 0.25 | 0.25 | 0.25 | 0.25 |
| Glycerin | 2.00 | 3.00 | 5.00 | 3.00 | 3.00 | 6.00 | 3.00 | 3.00 |
| Deionized Water | 13.00 | 13.00 | 13.00 | 13.00 | 13.00 | 13.00 | 11.00 | 17.00 |
| Betaine | 9.00 | 10.00 | 11.00 | 9.00 | 9.00 | 9.00 | 9.00 | 7.00 |
| Propylene Glycol | 2.00 | 2.00 | 3.00 | 2.00 | 2.00 | 3.00 | 2.00 | 2.00 |
| Caprylic/Capric Triglycerides | 1.00 | 1.00 | 1.00 | 2.00 | 1.00 | 2.00 | 1.00 | 1.00 |
| Sodium Lauryl Ether Sulphate (2 EO) (70% Active) | 18.42 | 18.42 | 16.42 | 18.42 | 18.42 | 12.42 | 22.42 | 18.42 |
| PHASE B | | | | | | | | |
| Glycerin USP | 3.00 | 3.00 | 3.00 | 3.00 | 3.00 | 3.00 | 3.00 | 3.00 |
| Jaguar C-13S | 0.50 | 0.50 | 0.50 | 0.50 | 0.50 | 0.50 | 0.50 | 0.50 |
| PHASE C | | | | | | | | |
| Tetrasodium EDTA (39% Active) | 0.02 | 0.02 | 0.02 | 0.02 | 0.02 | 0.02 | 0.02 | 0.02 |
| Glydant Liquid Plus | 0.10 | 0.10 | 0.10 | 0.10 | 0.10 | 0.10 | 0.10 | 0.10 |
| Vitamin E Acetate | 0.01 | 0.01 | 0.01 | 0.01 | 0.01 | 0.01 | 0.01 | 0.01 |
| Vitamin A Palmitate | 0.01 | 0.01 | 0.01 | 0.01 | 0.01 | 0.01 | 0.01 | 0.01 |
| Aloe Vera Gel | 0.10 | 0.10 | 0.10 | 0.10 | 0.10 | 0.10 | 0.10 | 0.10 |
| Green Tea Extract | 0.10 | 0.10 | 0.10 | 0.10 | 0.10 | 0.10 | 0.10 | 0.10 |
| Roman Chamomile Extract | 0.10 | 0.10 | 0.10 | 0.10 | 0.10 | 0.10 | 0.10 | 0.10 |
| Sunflower Seed Oil | 0.01 | 0.01 | 0.01 | 0.01 | 0.01 | 0.01 | 0.01 | 0.01 |
| Cholesterol | 0.01 | 0.01 | 0.01 | 0.01 | 0.01 | 0.01 | 0.01 | 0.01 |
| Mineral Oil | 3.00 | 2.00 | 2.00 | 2.00 | 3.00 | 3.00 | 5.00 | 3.00 |
| Fragrance | 2.00 | 3.00 | 2.00 | 2.00 | 2.00 | 2.00 | 2.00 | 2.00 |

The articles according to the Example when applied by a consumer to their body under shower conditions, will absorb water and expand. The resultant wiping article will be easier to handle and have a greater useful surface wiping area than similar formulated articles merely having roundapertured openings in the web.

EXAMPLES 9–15

The same nonwoven textile and application methods described under Examples 1–8 are used for the present set of experiments. Herein the cleansing compositions reported under Table II are deposited onto a nonwoven high-loft polyester substrate at a 1:1 weight ratio of composition to substrate.

TABLE II

| Ingredient | \multicolumn{7}{c}{Example (Weight %)} | | | | | | |
|---|---|---|---|---|---|---|---|
| | 9 | 10 | 11 | 12 | 13 | 14 | 15 |
| Hexylene Glycol | 15.00 | 13.45 | 11.00 | — | 19.45 | 29.00 | — |
| Butylene Glycol | — | 2.00 | 4.00 | 15.00 | — | — | 19.00 |
| Water | 25.00 | 25.00 | 25.00 | 25.00 | 25.00 | 30.00 | 30.00 |
| Polyquaternium (Polymer JR 400 ®) | 1.00 | — | — | — | — | — | — |
| PEG 9M (PEO-2) | — | — | — | 1.00 | — | — | 1.00 |
| Polyquaternium 4 (Celquat L-200 ®) | — | 0.15 | — | — | 0.15 | — | — |
| Polyquaternium 4 (Celquat L-230M ®) | — | 0.40 | — | — | 0.40 | — | — |
| Hydroxypropyl Cellulose (Klucel GF ®) | — | — | 1.00 | — | — | 1.00 | — |
| Polyquaternium 7 (Merquat 2200 ®) | 1.33 | 1.33 | 1.33 | 1.33 | — | — | — |
| Cocamidopropyl Betaine (Tegobetaine F ®; 30% Active) | 17.60 | 17.60 | 17.60 | 17.60 | 20.00 | 20.00 | 20.00 |
| Decyl Polyglucoside (Plantaren 2000N ®; 50% Active in Water) | 11.00 | 11.00 | 11.00 | 11.00 | 15.00 | — | — |
| Sodium Lauroyl Sarcosinate (Hamposyl L-30 ®; 30% Active) | 17.60 | 17.60 | 17.60 | 17.60 | 20.00 | 20.00 | 30.00 |
| Sodium Lauroyl Lactylate (Pationic 138C ®) | 1.74 | 1.74 | 1.74 | 1.74 | — | — | — |
| Capric/Caprylic Triglycerides (Miglyol 812 ®) | 2.50 | 2.50 | 2.50 | 2.50 | — | — | — |
| Silicone Quaternium-8 (Silquat AD ®; 40% Active in Water) | 6.00 | 6.00 | 6.00 | 6.00 | — | — | — |
| Fragrance | 1.03 | 1.03 | 1.03 | 1.03 | — | — | — |
| Glydant Plus ® Liquid (DMDM Hydantoin and Iodopropynyl Butylcarbamate in Butylene Glycol) | 0.20 | 0.20 | 0.20 | 0.20 | — | — | — |

What is claimed is:

1. A personal care cleansing article comprising;
   (i) a water insoluble synthetic fibered substrate formed of a web with a plurality of slits cut through and into the substrate and having a length ranging from about 6 to about 40 mm and a width no larger than about 2 mm; and
   (ii) a cleansing composition adjacent the substrate comprising from about 0.1% to about 95% of lathering surfactants by weight of the composition.

2. The article according to claim 1 wherein the substrate is lofty having a Loft-Soft Ratio greater than 1.1.

3. The article according to claim 1 wherein the slits have a length ranging from about 10 to about 25 mm.

4. The article according to claim 1 wherein the plurality of slits ranges in amount from about 10 to about 100.

5. The article according to claim 1 wherein the slits are straight linear and arranged in a direction parallel to a length of the substrate.

6. The article according to claim 1 wherein the slits have first and second arm members forming an angle from about 10 to about 150° arc therebetween.

7. The article according to claim 1 wherein the substrate has a web formed with both straight linear and angled slits.

8. The article according to claim 1 wherein the article has a water content ranging from about 20 to about 40% water by weight of the article.

9. The article according to claim 1 further comprising a plurality of icons embossed or printed on the web between the plurality of slits.

10. The article according to claim 1 wherein the icons are embossed.

11. The article according to claim 1 wherein the synthetic fibered substrate consists of a synthetic material selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof.

12. The article according to claim 1 wherein the substrate is formed from a blend of rayon/polyester in ratio of 10:90 to 90:10.

13. The article according to claim 1 wherein the slits have a length ranging from about 25 to about 40 mm.

14. The article according to claim 1 wherein the lathering surfactant is anionic and present in an amount ranging from about 5 to about 70% by weight of the cleansing composition.

* * * * *